United States Patent
Kumar et al.

(10) Patent No.: US 9,598,403 B2
(45) Date of Patent: Mar. 21, 2017

(54) PROCESS FOR THE PREPARATION OF RIVAROXABAN

(71) Applicant: Amneal Pharmaceuticals LLC, Bridgewater, NJ (US)

(72) Inventors: Agarwal Virendra Kumar, Gujarat (IN); Upadhyay Ashish Rameshchandra, Rajasthan (IN); Thumar Nilesh Mansukhlal, Gujarat (IN); Vala Hardevsinh Kanaksinh, Gujarat (IN)

(73) Assignee: Amneal Pharmaceuticals LLC, Bridgewater, NJ (US)

( * ) Notice: Subject to any disclaimer, the term of this patent is extended or adjusted under 35 U.S.C. 154(b) by 0 days.

(21) Appl. No.: 14/911,914

(22) PCT Filed: Aug. 19, 2014

(86) PCT No.: PCT/US2014/051583
§ 371 (c)(1),
(2) Date: Feb. 12, 2016

(87) PCT Pub. No.: WO2015/026761
PCT Pub. Date: Feb. 26, 2015

(65) Prior Publication Data
US 2016/0194309 A1    Jul. 7, 2016

(30) Foreign Application Priority Data
Aug. 19, 2013 (IN) .......................... 2699/MUM/2013

(51) Int. Cl.
*C07D 413/14* (2006.01)
*C07D 413/12* (2006.01)
*C07D 265/32* (2006.01)

(52) U.S. Cl.
CPC ......... *C07D 413/14* (2013.01); *C07D 265/32* (2013.01); *C07D 413/12* (2013.01)

(58) Field of Classification Search
None
See application file for complete search history.

(56) References Cited

U.S. PATENT DOCUMENTS

| 7,157,456 B2 | 1/2007 | Straub et al. |
| 7,816,355 B1 | 10/2010 | Bodhuri et al. |
| 8,106,192 B2 | 1/2012 | Thomas |

FOREIGN PATENT DOCUMENTS

| WO | WO-2012/051692 | 4/2012 |
| WO | WO-2013/046211 | 4/2013 |

OTHER PUBLICATIONS

PCT International Preliminary Report on Patentability in PCT/US2014/051583, dated Feb. 23, 2016, 6 pages.
PCT International Search Report in PCT/US2014/051583, mailed Nov. 27, 2014, 5 pages.
PCT International Written Opinion in PCT/US2014/051583, mailed Nov. 27, 2014, 5 pages.

*Primary Examiner* — Samantha Shterengarts
(74) *Attorney, Agent, or Firm* — Servilla Whitney LLC

(57) ABSTRACT

Described is an improved, industrially feasible and environmental friendly process for the preparation of Rivaroxaban. Also described are novel compounds which may be used as intermediates in preparation of Rivaroxaban.

10 Claims, No Drawings

PROCESS FOR THE PREPARATION OF RIVAROXABAN

CROSS-REFERENCE TO RELATED APPLICATIONS

This application is the National Stage entry of PCT/US 14/51583, filed on Aug. 19, 2014, which claims priority to Indian Application Number 2699/MUM/2013, filed on Aug. 19, 2013, which is incorporated herein by reference in their entireties.

TECHNICAL FIELD

The present invention relates to a process for preparation of 5-Chloro-N-({(5S)-2-oxo-3-[4-(3-oxo-4-morpholinyl)phenyl]-1,3-oxazolidin-5yl}methyl)-2-thiophenecarboxamide (Rivaroxaban) and intermediates thereof.

BACKGROUND

Rivaroxaban is an orally active factor Xa inhibitor developed by Bayer Healthcare for the prevention and treatment of deep vein thrombosis and pulmonary embolism in patients undergoing knee and hip replacement surgery. Rivaroxaban has an oxazolidinone nucleus and chemically is known as 5-Chloro-N-({(5S)-2-oxo-3-[4-(3-oxo-4-morpholinyl)phenyl]-1,3-oxazolidin-5yl}methyl)-2-thiophenecarboxamide, represented by the following structural formula:

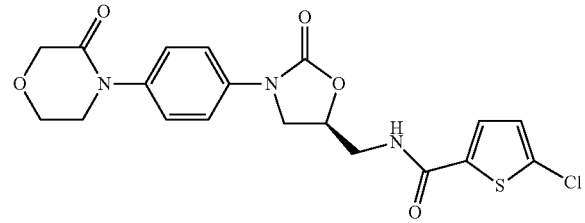 [SMILES: O=C(NC[C@H]1CN(c2ccc(N3CCOCC3=O)cc2)C(=O)O1)c1ccc(Cl)s1]

Currently, Rivaroxaban is marketed under trade name XARELTO® by Janssen Pharmaceuticals, Inc.

Rivaroxaban was first disclosed in U.S. Pat. No. 7,157,456 (herein, "the '456 patent"), where it is prepared by reacting 2-[(2S)-2-oxiranylmethyl]-1H-isoindole-1,3(2H)-dione (X) with 4-(4-aminophenyl)-3-morpholinone (II) to obtain 2-((2R)-2-hydroxy-3-{[4-(3-oxo-4-morpholinyl)phenyl]amino}propyl-1H-isoindole-1,3(2H)-dione (XI), as depicted in Scheme 1. The obtained compound is cyclized in the presence of dimethylaminopyridine, tetrahydrofuran and N,N'-carbonyldiimidazole to yield 2-({(5S)-2-oxo-3-[4-(3-oxo-4-morpholinyl)phenyl]-1,3-oxazolidin-5-yl}methyl)-1H-isoindole-1,3(2H)-dione (XII). Elimination of the phthalimide protective group affords compound (XIII), which is used, without further purification, in the last step of the synthetic route. Crude Rivaroxaban (I) is obtained by adding 5-chlorothiphene-2-carbonylchloride (VIII) to a solution of the compound XIII in pyridine. Purification of Rivaroxaban is carried out by means of flash chromatography.

The process of the '456 patent has several disadvantages, such as low yield, usage of expensive starting materials, and unwanted side reactions. The side reactions result in a final product of low purity, making chromatographic purification methods unavoidable and not feasible at an industrial scale. Additionally, the process involves the use of pyridine, which is a well known carcinogen, as a solvent and base.

Scheme I

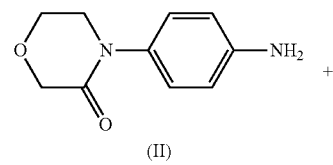

(II)

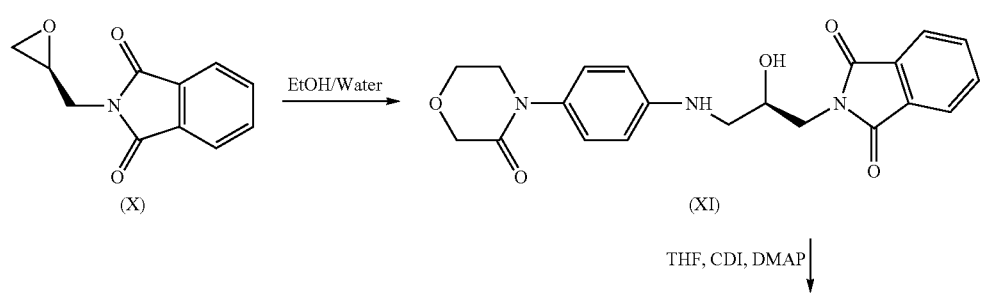

-continued

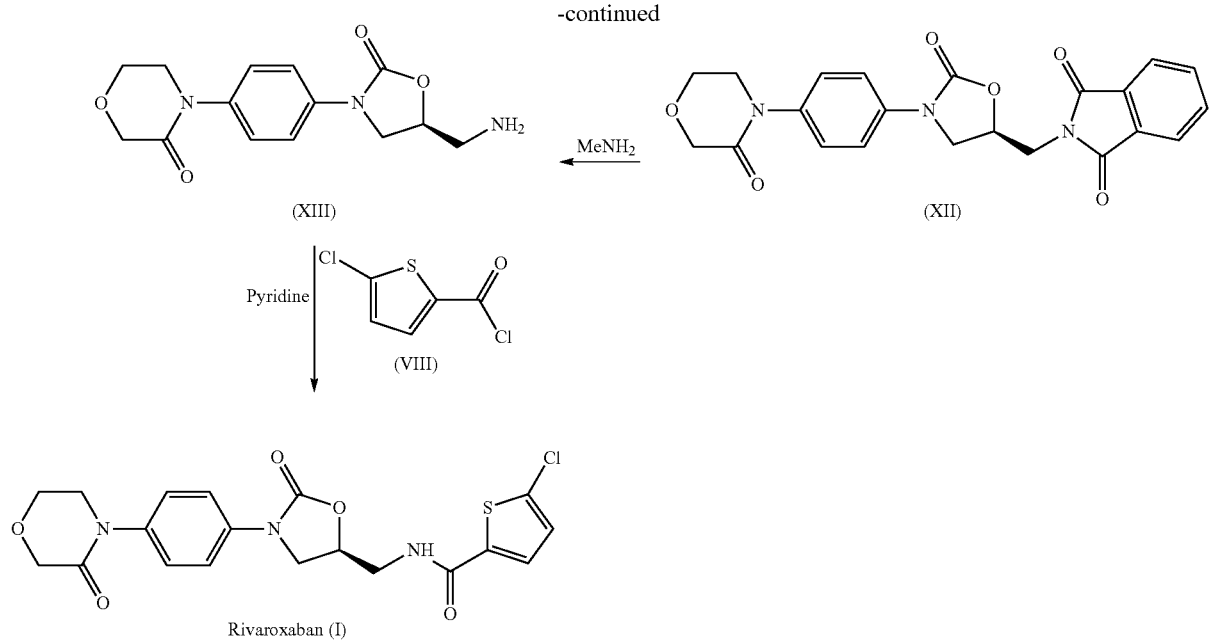

U.S. Pat. No. 8,106,192 (herein, "the '192 patent") describes another process for preparation of Rivaroxaban as shown in scheme II. In the process of the '192 patent, 5-chlorothiophene-2-carbonyl chloride (VIIIa) is reacted with (2S)-3-aminopropane-1,2-diol hydrochloride (XIV) to yield 5-chlorothiophene-2-carboxylic acid ((S)-2,3-dihydroxypropyl)-amide (XV), which is further brominated using a solution of 33% hydrobromic acid in acetic acid. The resulting bromo compound (XVI) is condensed with 4-(4-aminophenyl)-3-morpholinone (II) to yield N—{(R)-2-hydroxy-3-[4-(3-oxomorpholin-4-yl)phenyl amino]propyl}-5-chloro-thiophene-2-carboxamide (XVII), which is further cyclized to obtain Rivaroxaban (I) in the presence of 1-methyl-2-pyrrolidone and N,N-carbonyldiimidazole.

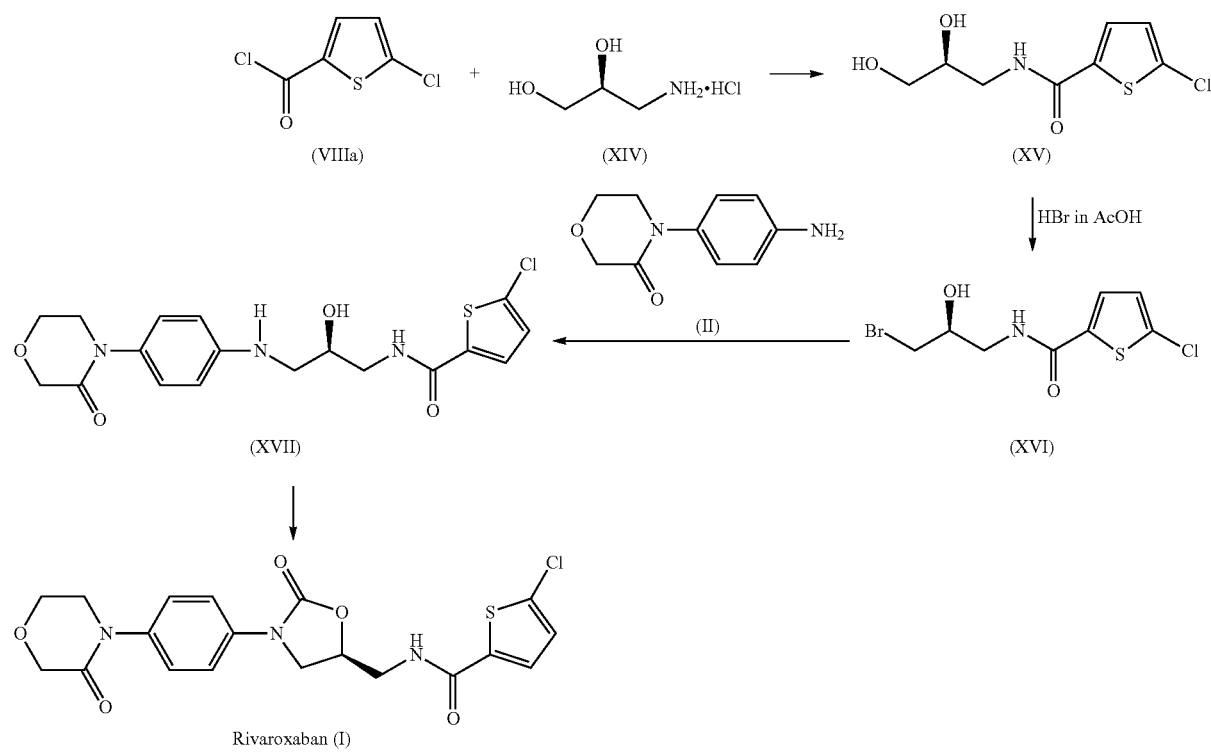

The process disclosed in the '192 patent involves the use of hazardous reagents, such as hydrobromic acid and N-methyl-2-pyrrolidone. N-methyl-2-pyrrolidone is known to be an irritant to skin and eyes and has also been identified as a reproductive toxicant. Thus, the process of the '192 patent is not feasible on an industrial scale.

Another process for the preparation of Rivaroxaban is described in U.S. Pat. No. 7,816,355 (herein, "the '355 patent"), as depicted in scheme III. The process involves the use of methyl N-(2R,3-epoxy-1-propyl)-N-[4-(3-oxo-4-morpholinyl)phenyl]carbamate (XX) as an intermediate for the synthesis of Rivaroxaban (I). This intermediate can be synthesized by reacting 4-(4-amino-phenyl)-morpholin-3-one (II) with (R)-(−)epichlorohydrine (III) to yield 4-[4-(N-(2R,3-epoxy-1-propyl)amino)phenyl]morpholin-3-one (XIX), which is further reacted with methyl chloroformate to provide said intermediate. Alternatively, this intermediate can be prepared by reacting 4-(4-amino-phenyl)-morpholin-3-one (II) with methyl chloroformate to give methyl N-[4-(3-oxo-4-morpholinyl)phenyl]carbamate (XVIII), which, on further reaction with (R)-(−)epichlorohydrine (III), provides said intermediate. The final step of the synthetic route involves condensation of this carbamate (XX) intermediate with 5-chlorothiophene-2-carboxamide (XXI) to yield Rivaroxaban (I).

The process disclosed in the '355 patent employs haloformates intermittently which are hazardous, corrosive and difficult to handle on an industrial scale.

In view of the above disadvantages of the prior art processes, there is a need to develop an improved process for the preparation of Rivaroxaban, which is industrially feasible and can avoid the use of potentially hazardous and expensive chemicals. Moreover, an improved process should avoid formation of isomeric and other process related impurities, while providing the desired product in high yield and purity.

SUMMARY

The present invention relates to processes for the preparation of 5-chloro-N-({(5S)-2-oxo-3-[4-(3-oxo-4-morpholinyl) phenyl]-1,3-oxazolidin-5-yl}methyl)-2-thiophenecarboxamide (I). In one aspect, the present invention provides a process for the preparation of Rivaroxaban (I)

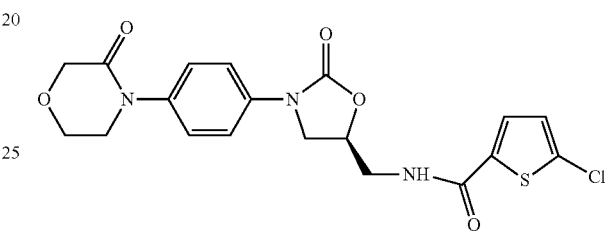

(I)

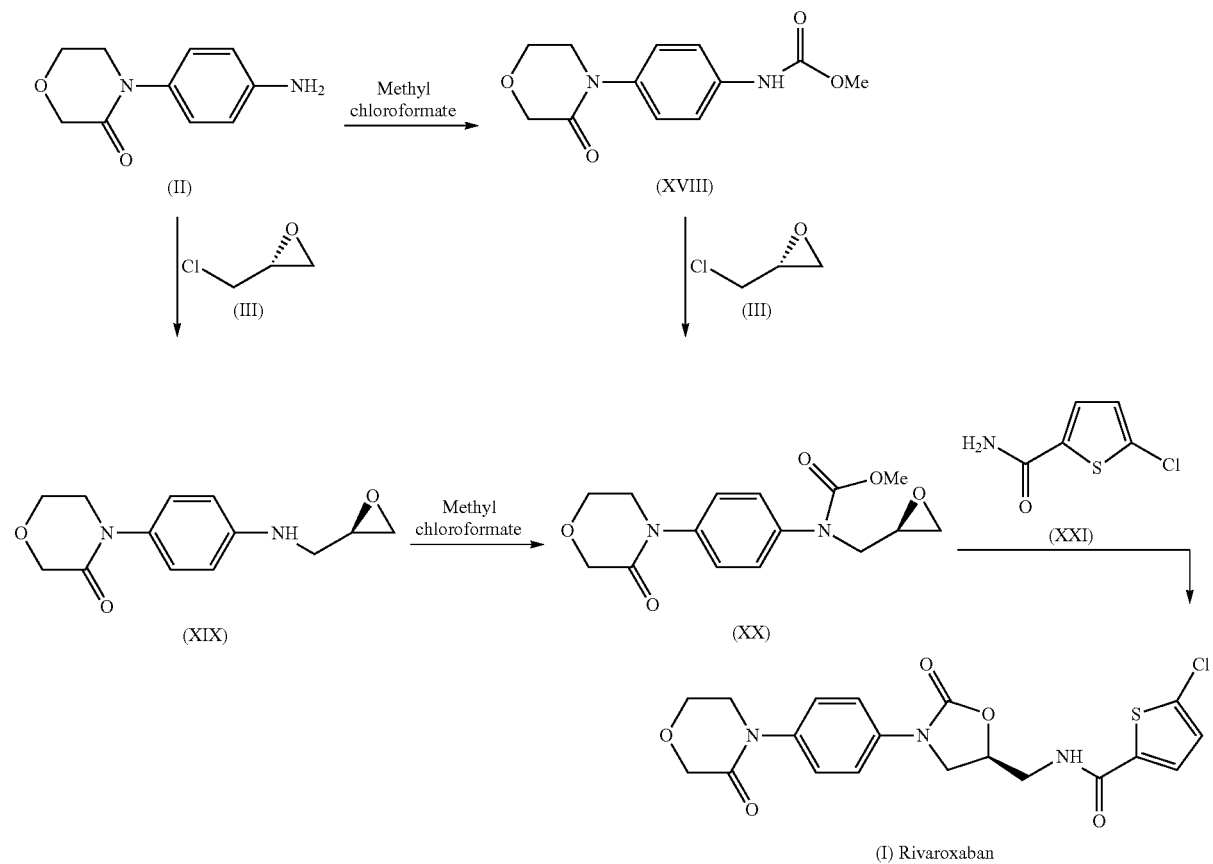

comprising:
a) reacting a compound of formula (IV)

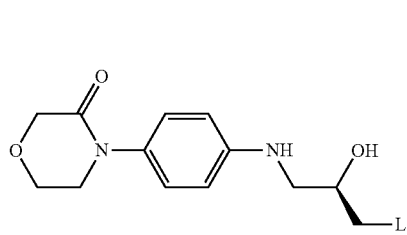
(IV)

with a compound G-L of formula (V), optionally in the presence of suitable base to give a compound of formula (VI)

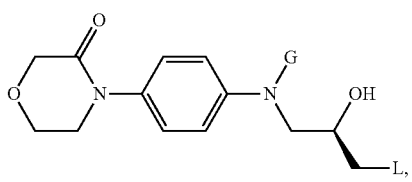
(VI)

wherein L is a leaving group and G is a protecting group;

b) converting the compound of formula (VI) to a compound of formula (VII) or salt thereof which may optionally involve isolation of a compound of formula (VII')

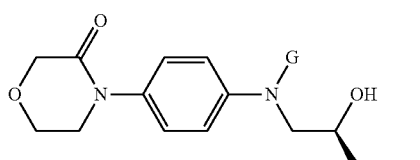
(VII)

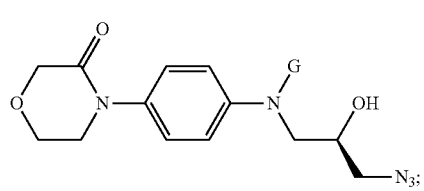
(VII')

c) reacting the compound of formula (VII) or salt thereof with 5-chloro thiophen-2-carboxylic acid or derivative (VIII)

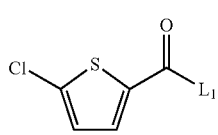
(VIII)

in the presence of a suitable base to give a compound of formula (IX)

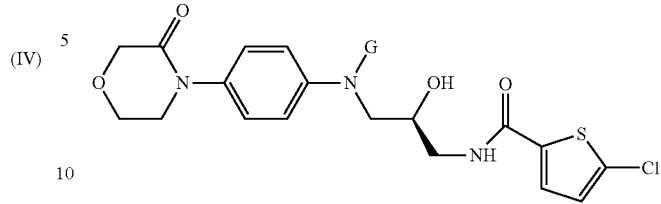
(IX)

wherein $L_1$ is a leaving group; and d) deprotecting and cyclizing the compound of formula (IX) to provide Rivaroxaban (I).

In another aspect, the present invention provides a process for the preparation of Rivaroxaban (I)

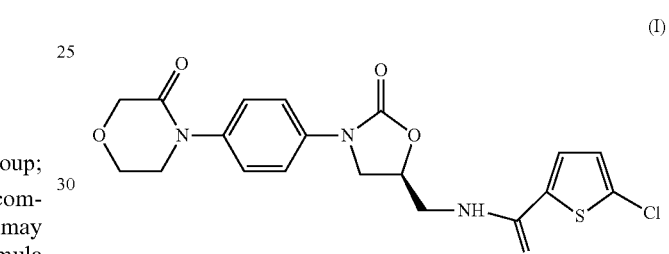
(I)

comprising:
a) reacting (R)-4-[4-(3-chloro-2-hydroxy propylamino)-phenyl]-morpholin-3-one (IVa)

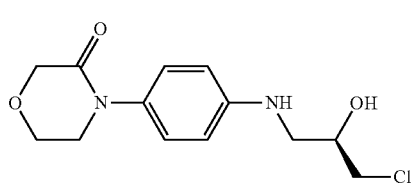
(IVa)

with benzyl bromide (Va) or benzyl chloride (Va')

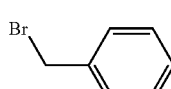
(Va)

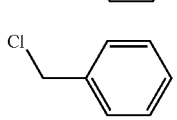
(Va')

optionally, in the presence of a suitable base, to give (R)-4-{4-[N-benzyl-(3-chloro-2-hydroxypropyl) amino]phenyl}-morpholin-3-one (VIa)

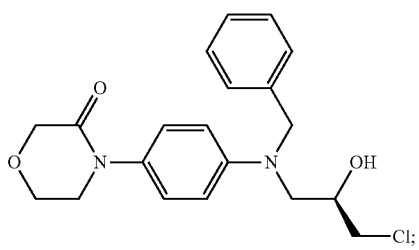
(VIa)

b) converting (R)-4-{4-[N-benzyl-(3-chloro-2-hydroxypropyl)amino]phenyl}-morpholin-3-one (VIa) to (S)-4-{4-[N-benzyl-(3-amino-2-hydroxypropyl)amino]phenyl}-morpholin-3-one phosphate (VIIaa) which may optionally involve isolation of (R)-4-{4-[N-benzyl-(3-azido-2-hydroxypropyl)amino]-phenyl}-morpholin-3-one (VII' a)

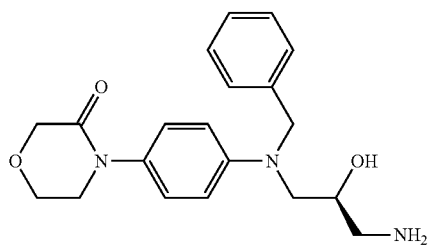
(VIIaa)

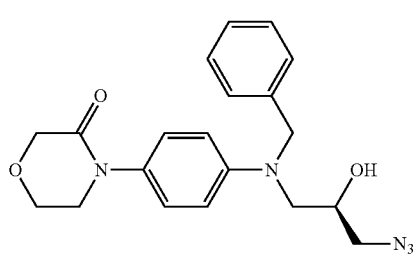
(VII'a)

c) reacting compound of formula (VIIaa) with 5-chlorothiophene-2-carbonyl chloride (VIIIa)

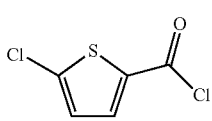
(VIIIa)

in the presence of a suitable base to give the compound of formula (IXa)

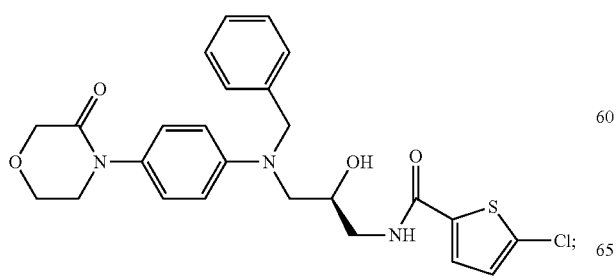
(IXa)

and d) deprotecting and cyclizing compound of formula (IXa) to provide Rivaroxaban (I).

The present invention further provides novel intermediates of formula (VI), (VII'), (VII), and (IX) and their salts or solvates thereof and their use in the preparation of Rivaroxaban (I).

In yet another aspect, the present invention further provides novel intermediates of formula (VIa), (VII' a), (VIIa) and (IXa) and their salts or solvates thereof and their use in preparation of Rivaroxaban (I).

In yet another aspect, the present invention further provides novel intermediate of formula (VIIaa).

DETAILED DESCRIPTION

According to one embodiment of the present invention, there is provided a process for preparation of Rivaroxaban (I) comprising steps of:

a) reacting a compound of formula (IV)

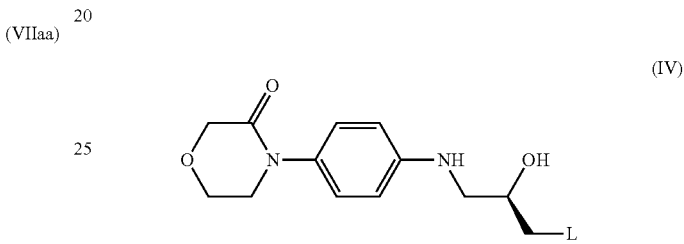
(IV)

with a compound G-L of formula (V) in the presence of a suitable base to give compound of formula (VI)

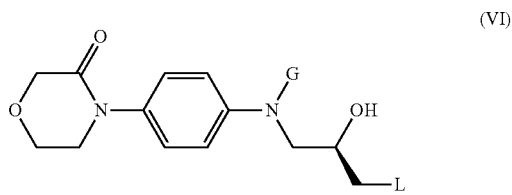
(VI)

wherein L is a leaving group selected from halogen or sulfonyloxy group, and G is a protecting group selected from —COR, —SO$_2$R, substituted or unsubstituted arylalkyl, substituted or unsubstituted C$_{4-10}$ alkyl and R is substituted or unsubstituted alkyl or substituted or unsubstituted aryl. The examples of G group include acetyl, propanoyl, butanoyl, mesyl, tosyl, p-nitrotosyl, benzyl, 4-methoxy benzyl, 4-nitro benzyl, 4-cyano benzyl, 4-methyl benzyl, 4-chlorobenzyl, trityl, diphenylmethyl, n-butyl, tert-butyl, isopentyl, tert-octyl and the like;

b) converting the compound of formula (VI) to a compound of formula (VII) or a salt thereof which may optionally involve isolation of a compound of formula (VII')

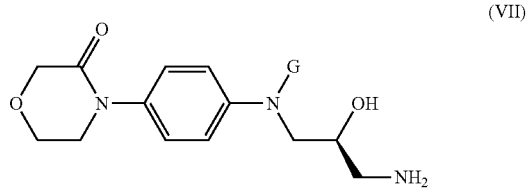
(VII)

-continued

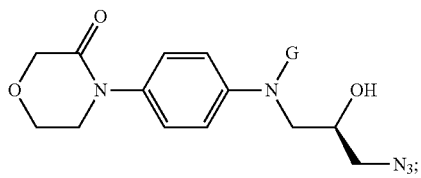
(VII')

c) reacting the compound of formula (VII) or a salt thereof with 5-chloro thiophen-2-carboxylic acid or a derivative of formula (VIII)

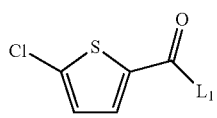
(VIII)

in the presence of a suitable base to give a compound of formula (IX)

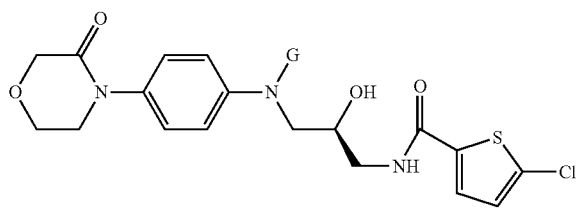
(IX)

wherein $L_1$ is a leaving group selected from the group consisting of halogen, sulfonyloxy, imidazole, ester, $C_{14}$ alkoxy, substituted $C_{14}$ alkoxy, trihalomethoxy, N-hydroxy succinimide, p-nitrophenol, N-hydroxy phthalimide, N-hydroxybenzotriazole and the like; and d) deprotecting and cyclizing the compound of formula (IX) to provide Rivaroxaban (I).

As used herein, the term "leaving group" can be defined as part of a substrate that is cleaved by the action of a nucleophile. As used herein, the term "alkyl" by itself, or as part of another substituent, means, unless otherwise stated, a saturated straight or branched chain, or cyclic hydrocarbon radical, or combination thereof having the number of carbon atoms designated (e.g., $C_{1-10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropy)methyl, homologs and isomers of, for example, n-pentyl, n-hexyl, n-heptyl, n-octyl, and the like.

As used herein, the term "aryl" by itself or as part of another substituent, means, unless otherwise stated, a polyunsaturated, aromatic, hydrocarbon substituent which can be a single ring or multiple rings (often from 1 to 3 rings) which are fused together or linked covalently. "Aryl" includes, but is not limited to, heteroaryl groups. Non-limiting examples of aryl and heteroaryl groups include: phenyl, 1-naphthyl, 2-naphthyl, 4-biphenyl, pyrrolyl, pyrazolyl, imidazolyl, pyrazinyl, oxazolyl, isoxazolyl, thiazolyl, furyl, thienyl, pyridinyl, benzothiazolyl, purinyl, benzimidazolyl, indolyl, isoquinolyl, quinoxalinyl, and quinolyl.

The base used in the present invention can be an inorganic or an organic base. Examples of organic bases include, but are not limited to, amines such as diisopropylethylamine (DIPEA), triethylamine (TEA), diethylamine (DEA), pyridine, 1,8-diazabicyclo[5.4.0]undec-7-ene (DBU), imidazole, N,N-dimethyl aniline, N,N-dimethyl amino pyridine (DMAP), 1,5-diazabicyclo[4.3.0]non-5-ene (DBN), n-butyl lithium, lithium diisopropylamide (LDA), lithium hexamethyldisilazide (LiHMDS), sodium hexamethyldisilazide (NaHMDS), potassium hexamethyldisilazide (KHMDS) and the like or mixtures thereof. Examples of inorganic bases include, but are not limited to alkali or alkaline earth metal carbonate, bicarbonate, hydroxide or phosphate such as potassium carbonate, sodium carbonate, lithium carbonate, sodium bicarbonate, potassium bicarbonate, lithium bicarbonate, sodium hydroxide, potassium hydroxide, lithium hydroxide, potassium phosphate, sodium phosphate, hydride such as sodium hydride, lithium hydride or potassium hydride, alkoxide such as sodium or potassium methoxide or ethoxide, tertiary butoxide and the like or mixtures thereof.

In another aspect, the present invention provides a process for the preparation of Rivaroxaban (I)

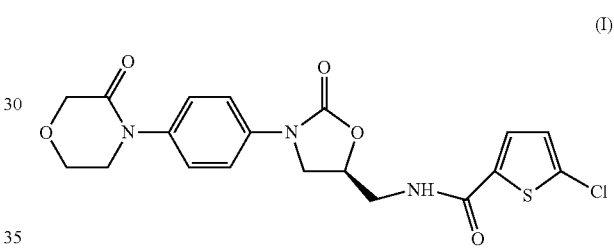
(I)

comprising:

a) reacting (R)-4-[4-(3-chloro-2-hydroxy propylamino)-phenyl]-morpholin-3-one (IVa)

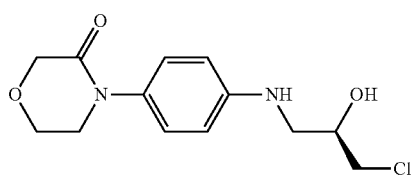
(IVa)

with benzyl bromide (Va) or benzyl chloride (Va')

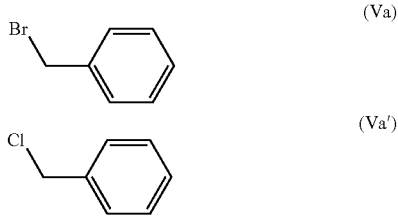
(Va)

(Va')

optionally, in the presence of a suitable base, to give (R)-4-{4-[N-benzyl-(3-chloro-2-hydroxypropyl) amino]phenyl}-morpholin-3-one (VIa)

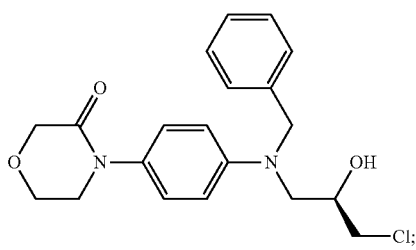
(VIa)

b) converting (R)-4-{4-[N-benzyl-(3-chloro-2-hydroxypropyl)amino]phenyl}-morpholin-3-one (VIa) to (S)-4-{4-[N-benzyl-(3-amino-2-hydroxypropyl)amino]phenyl}-morpholin-3-one (VIIa) or pharmaceutically acceptable salt thereof, which may optionally involve isolation of (R)-{4-[N-benzyl-(3-azido-2-hydroxypropyl)amino]-phenyl}-morpholin-3-one (VII' a)

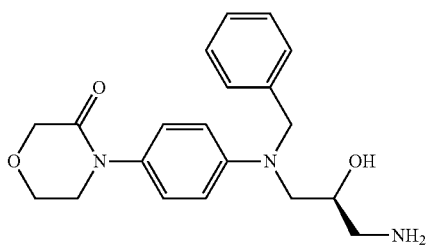
(VIIa)

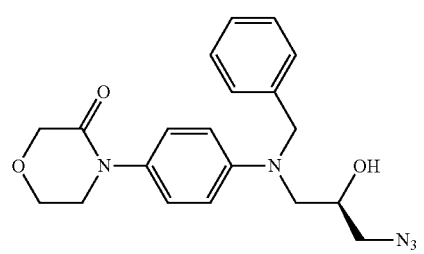
(VII'a)

c) reacting a compound of formula (VIIa) or a pharmaceutically acceptable salt, with 5-chlorothiophene-2-carbonyl chloride (VIIIa)

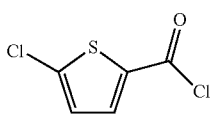
(VIIIa)

in the presence of a suitable base to give the compound of formula (IXa)

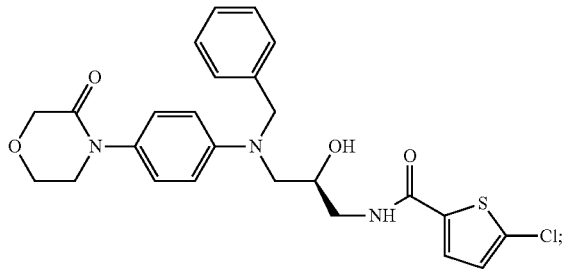
(IXa)

and d) deprotecting and cyclizing the compound of formula (IXa) to provide Rivaroxaban (I).

According to another embodiment of the present invention, a compound of formula (IVa) can be prepared by reacting (R)-Epichlorhydrin with 4-(4-aminophenyl)-morpholin-3-one in the presence of an alcoholic solvent selected from the group consisting of methanol, ethanol, isopropanol, n-propanol, isobutanol, tert-butanol or mixtures thereof.

According to another embodiment of the present invention, provided is a process for the preparation of a novel intermediate of formula (VI) and its use in the preparation of Rivaroxaban (I). The process comprises reacting a compound of formula (IV) with a compound of formula (V) in an organic solvent and in the presence of a base to give the compound of formula (VI).

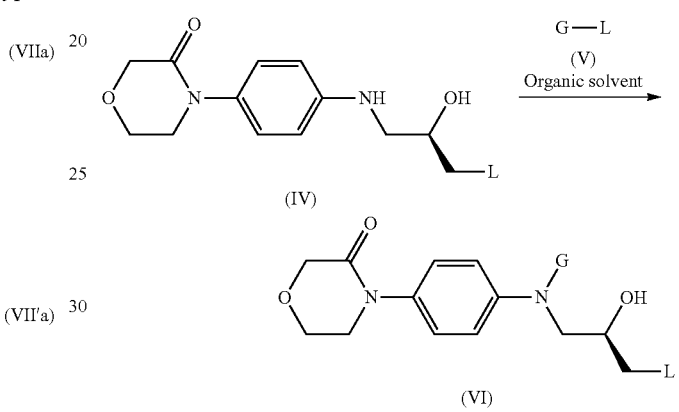

Examples of the compound of formula (V) include, but are not limited to, benzyl bromide, benzyl chloride, acetyl chloride, mesyl chloride, tosyl chloride, trityl chloride, 4-nitro benzyl chloride, 4-methoxy benzyl tosylate, benzyl mesylate and the like.

Organic solvents used for this step can be selected from esters such as ethyl acetate, methyl acetate, butyl acetate, isopropylacetate, nitriles such as acetonitrile, propionitrile, butyronitrile, benzonitrile, hydrocarbons such as toluene, xylene, chlorinated hydrocarbons such as dichloromethane, ethylene dichloride, chlorobenzene, chloroform, ketones such as acetone, methyl ethyl ketone (MEK), methyl isobutyl ketone (MIBK), polar aprotic solvents such as N,N-dimethylformamide (DMF), dimethyl acetamide (DMAc), dimethyl sulfoxide (DMSO), sulfolane, water, or mixtures thereof.

Bases used for this step can be selected from inorganic and organic bases, as defined above, for example, organic amines such as DIPEA (diisopropylethyl amine), TEA (triethyl amine), DEA (diethyl), pyridine, DBU, imidazole, N,N-dimethyl aniline, DMAP, and the like, or mixtures thereof.

According to another embodiment of the present invention, there is provided a process for the preparation of a novel intermediate of formula (VII) and its use in the preparation of Rivaroxaban (I). The process comprises reacting a compound of formula (VI) with alkali azide such as sodium azide or potassium azide, in an organic solvent at reflux temperature preferably at 70-120° C., or more preferably at 100-110° C., for 6-8 hours, to give an azide intermediate of formula (VII'). In situ reduction of this azide intermediate gives a compound of formula (VII).

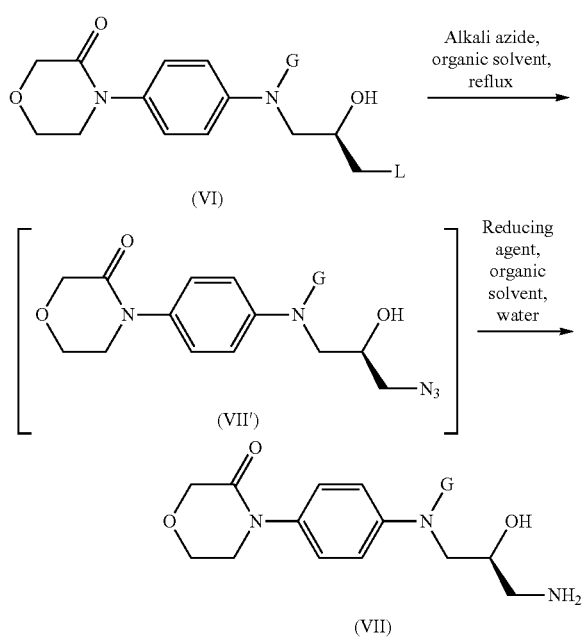

Organic solvents used for this step can be selected from groups comprising polar aprotic solvents such as DMF, DMAc, DMSO; hydrocarbons such as toluene or xylene; nitriles such as acetontrile; ethers such as tetrahydrofuran (THF), water; and the like. A mixture of solvents or solvent with water can also be used. Reduction of azide intermediate (VII') can be performed by catalytic hydrogenation using noble metal catalysts such as Pd, Pt, Rh, Ru supported on carbon, or using a complex of such metal. Alternatively, azide can also be reduced using triphenylphosphine.

Yet another embodiment of the present invention involves isolation of the azide intermediate (VII'), followed by reduction to give a compound of formula (VII). According to another embodiment of present invention, provided is a process for the preparation of a novel intermediate of formula (IX) and its use in the preparation of Rivaroxaban (I), which comprises reacting a compound of formula (VII) with a compound of formula (VIII) in the presence of a base and organic solvent to give the compound of formula (IX).

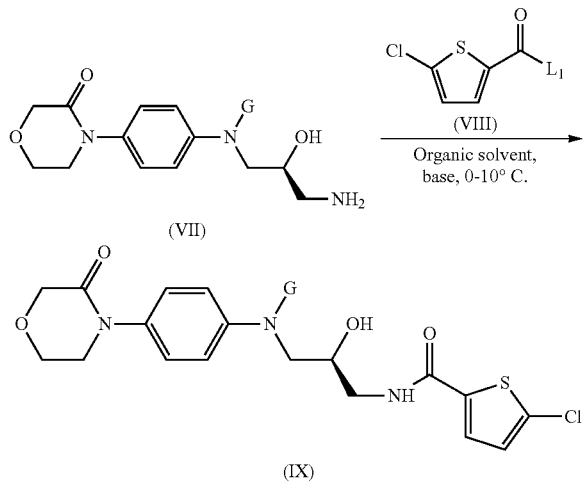

Non-limiting examples of the compound of formula (VIII) include 5-chloro thiophen-2-carboxylic acid, the corresponding carbonyl halide, symmetric or mixed carboxylic mixed anhydride, the corresponding sulfonyloxy or imidazole derivatives.

Organic solvents used for this step include, but are not limited to, chlorinated solvents such as dichloromethane, dichloroethane, chloroform, and chlorobenzene. Bases used for this step are selected from DIPEA, TEA, DEA, pyridine, DMAP, DBU, N,N-dimethyl aniline, potassium carbonate, sodium carbonate, lithium carbonate, sodium bicarbonate, potassium bicarbonate, lithium bicarbonate or mixtures thereof.

When 5-chlorothiophen-2-carboxylic acid is used as compound (VIII), reaction can be carried out using condensing agents such as CDI (carbonyldiimidizole), HOBt (1-Hydroxybenzotriazole), HATU ((O-(7-azabenzotriazol-1-yl)-N,N,N',N'-tetramethyluronium hexafluorophosphate)), TATU ((O-(7-Azabenzotriazole-1-yl)-N,N,N',N'-tetramethyluronium tetrafluoroborate)), EDC (1-Ethyl-3-(3-dimethylaminopropyl)carbodiimide), DCC (N,N'-Dicyclohexylcarbodiimide) in organic solvent, optionally in the presence of a base.

According to an another embodiment of present invention, provided is a process for converting the compound of formula (IX) to Rivaroxaban (I), which comprises a single step deprotection and cyclization of the compound of formula (IX), using phosgene equivalents to yield Rivaroxaban (I).

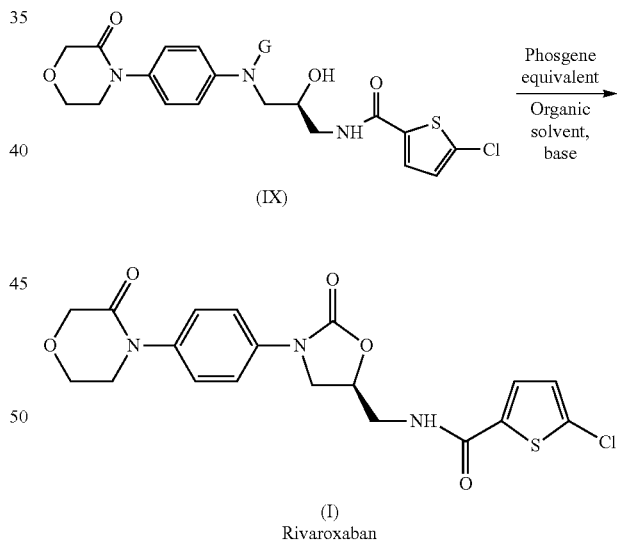

As used herein, the term "phosgene equivalent" refers to any reagent which imparts a carbonyl group to the reactant. Examples of phosgene equivalents include triphosgene, carbonyl diimidazole (CDI), dicyclohexyl carbodiimide (DCC), and the like.

Organic solvents used for this step include, but are not limited to, chlorinated hydrocarbons or ketones. Examples of bases include, but are not limited to, alkali or alkaline earth metal carbonates or bicarbonates, ammonia or ammonium salts.

Yet another embodiment of the present invention involves an alternate process for converting the compound of formula (IX) to Rivaroxaban (I). The process comprises isolation of a deprotected intermediate (IX'), which is further cyclized to yield Rivaroxaban (I).

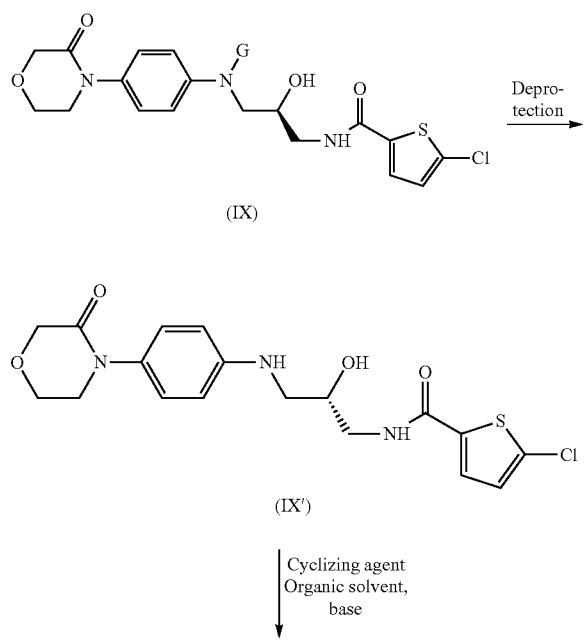

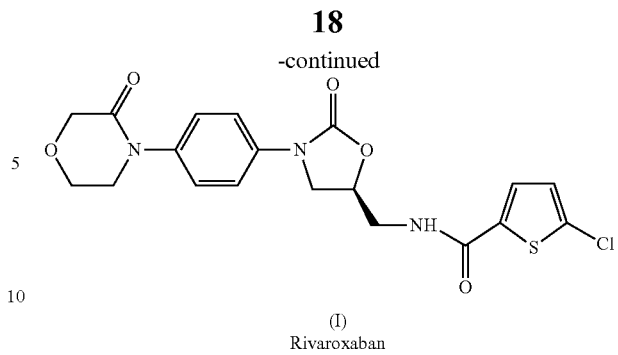

The present invention further provides novel intermediates of formula (VI), (VII'), (VII), and (IX) and their salts or solvates thereof, and their use in the preparation of Rivaroxaban (I).

In yet another aspect, the present invention further provides novel intermediates of formula (VIa), (VII' a), (VIIa) and (IXa) and their salts or solvates thereof, and their use in the preparation of Rivaroxaban (I). In yet another aspect, the present invention further provides a novel intermediate of formula (VIIaa).

According to another embodiment of present invention, the compound of formula (VI) can be converted to a compound of formula (VII), by reacting the compound of formula (VI) with ammonia or phthalimide, and succimide, or derivatives thereof, followed by reduction.

In one embodiment, the synthetic reaction scheme of the present invention is as shown in Scheme-IV.

Scheme IV

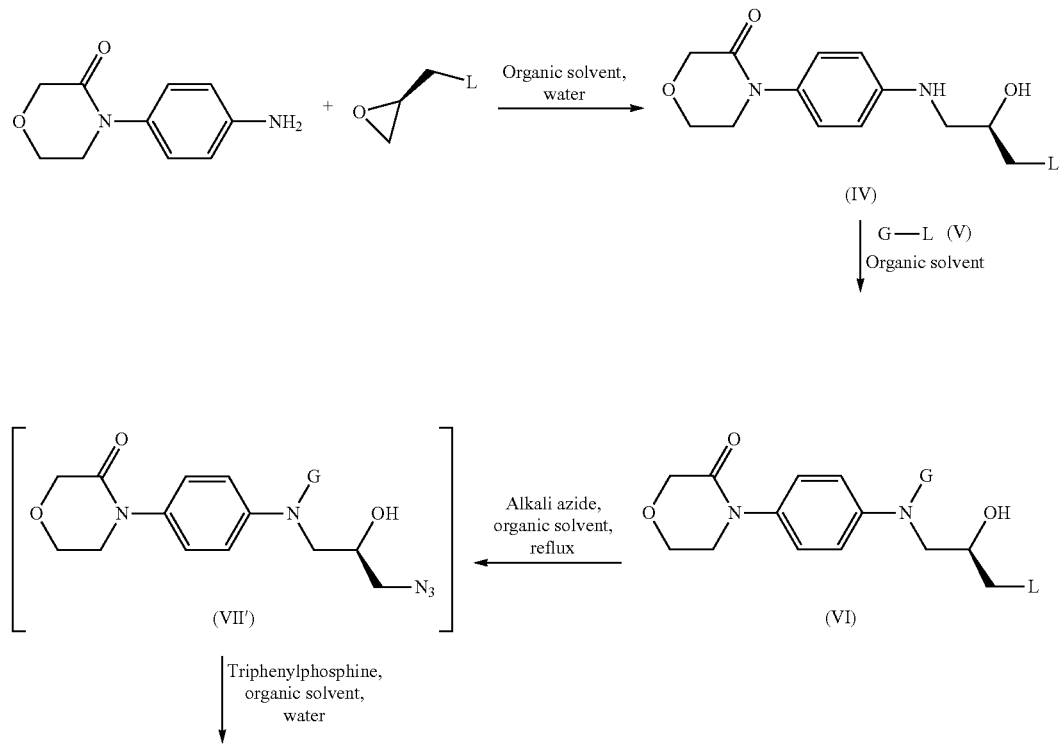

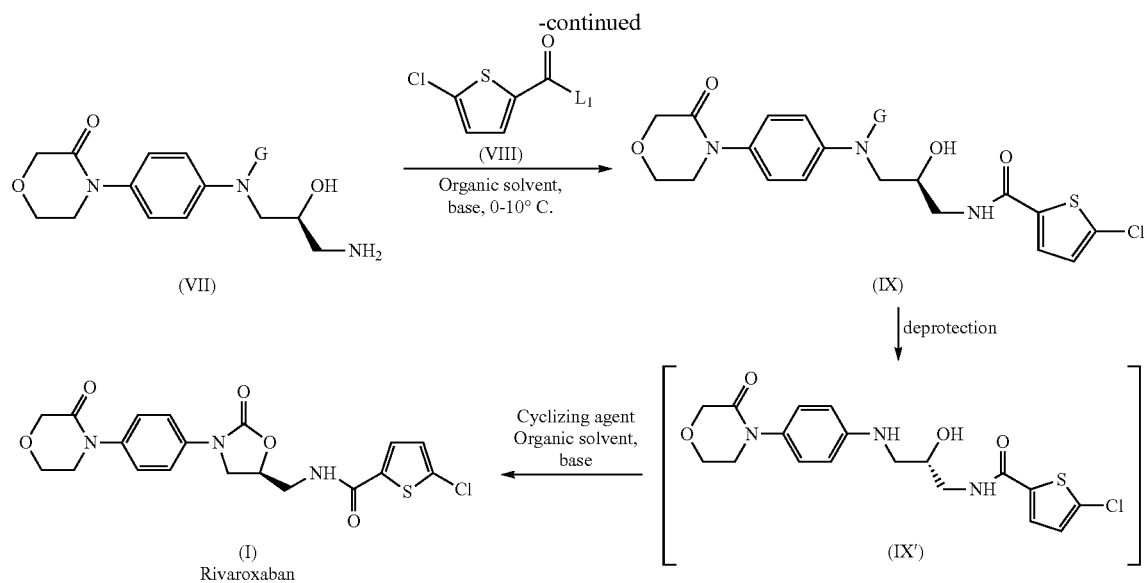
In another embodiment of the present invention, the synthetic route can be depicted as shown in Scheme-IV'.
Scheme IV'
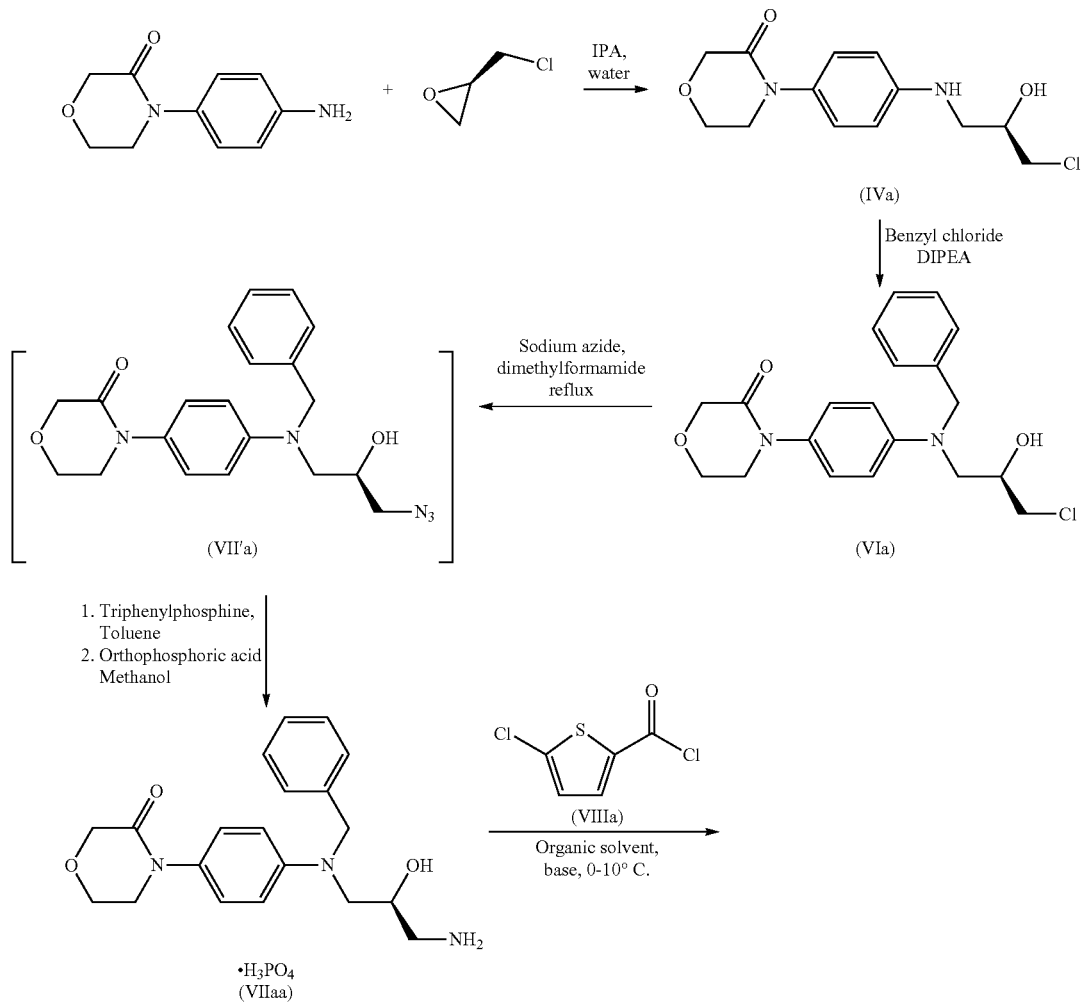

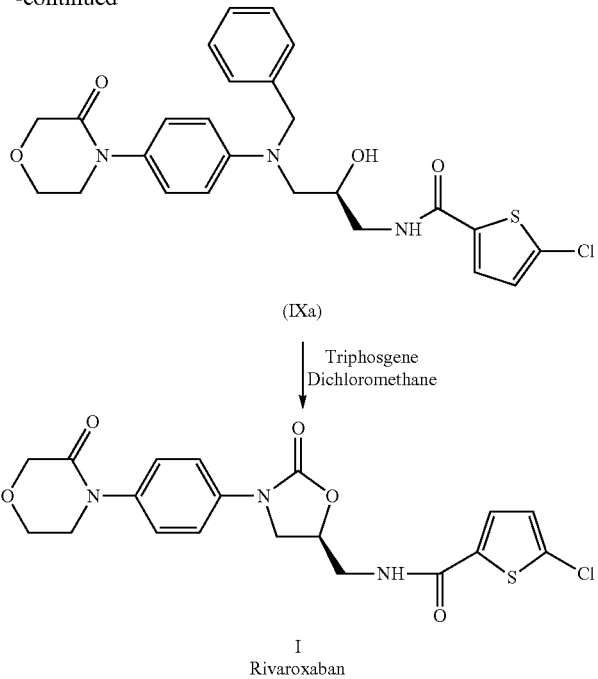

(IXa)

Triphosgene
Dichloromethane

I
Rivaroxaban

The following examples are given for the purpose of illustrating the present invention and should not be considered as limiting the scope of the invention.

Example 1

Preparation of (R)-4-[4-(3-chloro-2-hydroxy propylamino)-phenyl]-morpholin-3-one (IVa)

R-epichlorohydrine (60.3 g; 0.65 mol) was added to a heterogeneous mixture of 4-(4-amino-phenyl)-morpholin-3-one (100 gm; 0.52 mol) in water (400 ml) and ethanol (100 ml) at 25-35° C. within 1 hour. The reaction mass was stirred at 25-35° C. for 12 hours. The resulting suspension was filtered and washed twice with ethanol:water (2:8). The solid was dried at 25-35° C. for 2 hours and then at 45-55° C. for 8 hours to give the title product (110-130 g). Yield: 80.0%

$^1$H NMR (DMSO) δ: 3.0-3.07 (1H, m), 3.15-3.21 (1H, m), 3.58-3.71 (4H, m), 3.82-3.86 (1H, q), 3.91-3.93 (2H, t), 4.13 (2H, s), 5.36-5.37 (1H, d), 5.72-5.75 (1H, t), 6.59-6.61 (2H, d), 7.02-7.04 (2H, d)

Mass: 285.1 [M+H]$^+$

Example 2

Preparation of (R)-4-[4-(3-chloro-2-hydroxypropylamino)-phenyl]-morpholin-3-one (IVa)

R-Epichlorohydrin (60.3 g; 0.65 mol) was added to a heterogeneous mixture of 4-(4-aminophenyl)-morpholin-3-one (100 g; 0.52 mol) in water (400 ml) and isopropyl alcohol (100 ml) at 25-35° C. within 1 hour. The reaction mass was stirred at 25-35° C. for 16 hours. The suspension was filtered and washed twice with 100 ml isopropyl alcohol:water (2:8) mixture. The solid was dried at 25-35° C. for 2 hours, at 35-55° C. for 2 hours and then at 50-60° C. for 12 hours. The solid was added in isopropyl alcohol (300 ml) at 25-35° C. The reaction mass was stirred at 25-35° C. for 2 hours. The suspension was filtered and washed with isopropyl alcohol (100 ml×4). The solid obtained was dried at 25-35° C. for 2 hours, at 35-55° C. for 2 hours and then at 50-60° C. for 12 hours to give the title product (80-100 g). Yield: 90%. HPLC Purity: 98.95%.

$^1$H NMR (DMSO) δ: 3.0-3.07 (1H, m), 3.15-3.21 (1H, m), 3.58-3.71 (4H, m), 3.82-3.86 (1H, q), 3.91-3.93 (2H, t), 4.13 (2H, s), 5.36-5.37 (1H, d), 5.72-5.75 (1H, t), 6.59-6.61 (2H, d), 7.02-7.04 (2H, d)

Mass: 285.1 [M+H]$^+$

Example 3

Preparation of (R)-4-{4-[N-benzyl-(3-chloro-2-hydroxypropyl)amino]-phenyl}-morpholin-3-one (VIa)

Benzyl bromide (Va) (75.0 g; 0.44 mol) was added to a mixture of (R)-4-[4-(3-chloro-2-hydroxy propylamino)-phenyl]-morpholin-3-one (IVa) (100.0 g; 0.35 mol), DMF (500 ml) and diisopropylethylamine (56.7 g; 0.44 mol) at 25-35° C. within 2 to 3 hours. The reaction mixture was heated at 45-55° C. for 3 hours. The reaction mixture was diluted with water and cooled to 25-35° C. The resulting solid was filtered and washed two times with water (50 ml). The solid was dried at 25-35° C. for 2 hours and then at 45-55° C. for 8 hours to give the title product (110-130 g). Yield: 85.0%.

$^1$H NMR (DMSO) δ: 3.42-3.47 (1H, m), 3.51-3.55 (1H, m), 3.58-3.72 (4H, m), 3.90-3.93 (2H, q), 3.99-4.1 (1H, m), 4.13-4.15 (2H, s), 4.61-4.72 (2H, q), 5.44-5.46 (1H, d), 6.67-6.70, (2H, d), 7.05-7.09 (2H, d), 7.19-7.24 (3H, m), 7.29-7.33 (2H, m)

Mass: 375.1[M+H]$^+$

Example 4

Preparation of (R)-4-{4-[N-benzyl-(3-chloro-2-hydroxypropyl)amino]-phenyl}-morpholin-3-one (VIa)

Benzyl chloride (Va') (55.5 g; 0.44 mol) was added to a mixture of (R)-4-[4-(3-chloro-2-hydroxy propylamino)-phenyl]-morpholin-3-one (IVa) (100.0 g; 0.35 mol), DMF (300 ml), diisopropyl ethyl amine (56.7 g; 0044 mol) and potassium iodide (17.5 g; 0.11 mol) at 25-35° C. The reaction mixture was heated at 60-70° C. for 8 hours. After completion of reaction, the reaction mixture was cooled to 20-30° C. and added triethylamine (53.3 g; 0.51 mol) within 1 hour. The reaction mass was stirred at 20-30° C. for 2 hours. Water (1500 ml) was added to the reaction mixture at 20-30° C. within 4 hours. The reaction mass was stirred at 20-30° C. for 2 hours. The resulting solid was filtered and washed with water (200 ml×4). The solid was dried at 25-35° C. for 2 hours, at 35-55° C. for 2 hours, at 45-55° C. for 2 hours, at 55-65° C. for 2 hours and then at 65-75° C. 12 hours to give the title product (115-130 g). Yield: 93.0%. HPLC Purity: 96.0%.

$^1$H NMR (DMSO) δ: 3.42-3.47 (1H, m), 3.51-3.55 (1H, m), 3.58-3.72 (4H, m), 3.90-3.93 (2H, q), 3.99-4.1 (1H, m), 4.13-4.15 (2H, s), 4.61-4.72 (2H, q), 5.44-5.46 (1H, d), 6.67-6.70, (2H, d), 7.05-7.09 (2H, d), 7.19-7.24 (3H, m), 7.29-7.33 (2H, m)

Mass: 375.1[M+H]$^+$

Example 5

Preparation of (S)-4-[4-[N-benzyl-(3-amino-2-hydroxypropyl)amino]-phenyl]-morpholin-3-one (VIIa)

A mixture of (R)-4-{4-[N-benzyl-(3-chloro-2-hydroxy propyl) amino]-phenyl}-morpholin-3-one (VIa) (100 g; 0.27 mol), N,N-dimethylformamide (300 ml), water (6.0 ml) and sodium azide (34.7 gm; 0.53 mol) was heated at 100-110° C. for 6 hours. After completion of reaction, the reaction mixture was cooled to 25-35° C. and was added to a mixture of water (1500 ml) and toluene (500 ml). The organic phase was separated and washed twice with water (200 ml). Water (100 ml) was added to the organic phase and heated at 50-60° C. A clear solution of triphenylphosphine (70.0 g; 0.27 mol) in toluene (500 ml) was added to the reaction mixture at 50-60° C. within 1-2 hours and stirred further for 3 hours. After completion of the reaction, the reaction mixture was cooled to 25-35° C. for 1 hour. The resulting solid was filtered, washed twice with toluene (50 ml) and dried at 25-35° C. for 2 hours and then at 45-55° C. for 8 hours to give the title product (70-85 g). Yield: 80.0%.

$^1$H NMR (DMSO) δ: 2.59-2.64 (1H, dd), 2.87-2.91 (1H, dd), 3.46-3.47 (2H, d), 3.66-3.68 (2H, t), 3.88-3.94 (1H, m), 3.98-4.00 (2H, m), 4.31 (2H, s), 4.60.4.70 (2H, q), 6.74-6.78 (2H, m), 7.07-7.11 (2H, m), 7.18-7.26 (3H, m), 7.29-7.33 (2H, t)

Mass: 355.9 [M+H]$^+$

Example 6

Preparation of (R)-4-{4-[N-benzyl-(3-azido-2-hydroxypropyl)amino]-phenyl}-morpholin-3-one (VII'a)

To a stirred mixture of (R)-4-{4-[N-benzyl-(3-chloro-2-hydroxy propyl) amino]-phenyl}-morpholin-3-one (VIa) (20 g; 0.05 mol), N,N-dimethylformamide (60 ml) and water (1.2 ml), sodium azide (6.94 gm; 0.10 mol) was added and heated at 100-110° C. for 6 hours. After completion of reaction, the reaction mixture was cooled to 25-35° C. and was added to a mixture of water (300 ml) and toluene (100 ml) for up to 1 hour and allowed to stir for further 20 minutes. Reaction mixture was allowed to separate into layers. The organic phase was separated and washed twice with water (40 ml). Organic phase was distilled out under vacuum below 60° C. to isolate azide intermediate in the form of residue (20.0 g). Yield: 97.0%.

$^1$H NMR (DMSO) δ: 3.25-3.29 (1H, m), 3.37-3.38 (1H, d), 3.44-3.61 (4H, m), 3.90-3.92 (2H, t), 4.00-4.04 (1H, m), 4.13 (2H, s), 4.58.4.69 (2H, q),4.45.4.47 (1H, d), 6.66-6.68, (2H, d), 7.05-7.07 (2H, d), 7.21-7.23 (3H, m), 7.29-7.33 (2H, m)

Mass: 382.2 [M+H]$^+$

Example 7

Preparation of (S)-4-[4-[N-benzyl-(3-amino-2-hydroxypropyl)amino]-phenyl]-morpholin-3-one phosphate (VIIaa)

A mixture of (R)-4-{4-[N-benzyl-(3-chloro-2-hydroxy propyl) amino]-phenyl}-morpholin-3-one (100 g; 0.27 mol), N,N-dimethylformamide (300 ml) and sodium azide (34.7 g; 0.53 mol) was heated at 80-90° C. for 6 hours. After completion of the reaction, the reaction mixture was cooled to 25-35° C. and diluted with toluene (700 ml). Water (1500 ml) was added to the reaction mixture at 25-35° C. for up to 2 hours. The reaction mass was stirred at 25-35° C. for 30 minutes and then allowed to settle. The organic phase was separated and washed with water (300 ml). Water (100 ml) was added to the organic phase and heated at 50-60° C. A clear solution of triphenylphosphine (70.0 g; 0.27 mol) in toluene (300 ml) was added to the reaction mixture at 50-60° C. for up to 1-2 hours and stirred further for 4 hours. After completion of reaction, the reaction mixture was cooled to 25-35° C. and stirred for 2 hours. The resulting solid was filtered and washed twice with toluene (50 ml). The isolated solid was dissolved in methanol (1200 ml) at 50-60° C. A clear solution of ortho phosphoric acid (27.7 g; 0.24 mol) in methanol (200 ml) was added to the reaction mixture at 50-60° C. within 1 hour and stirred further for 2 hours. After completion of the reaction, the reaction mixture was cooled to 25-35° C. and stirred for 2 hours. The resulting solid was filtered and washed with methanol (25 ml×4). The solid was dried at 25-35° C. for 2 hours and then at 70-80° C. 12 hours to give the title product (65-75 g). Yield: 74.0%. HPLC Purity: 99.7%.

$^1$H NMR (DMSO) δ: 2.77-2.83 (1H, t), 3.01-3.04 (1H, d), 3.54-3.55 (2H, d), 3.60-3.62 (2H, t), 3.92-3.95 (2H, t), 4.07-4.09 (1H, d), 4.15 (2H, s), 4.68 (2H, s), 6.71-6.74 (2H, d), 7.08-7.10 (2H, d), 7.17-7.25 (3H, m), 7.31-7.34 (2H, t), 7.76 (2H, s)

Mass: 354.2 [M-(H$_3$PO$_4$)—H]$^-$

Example 8

Preparation of (S)-5-chloro-thiophene-2-carboxylic acid (3-{N-benzyl-[4-(3-oxo-morpholin-4-yl)-phenyl]-amino}-2-hydroxy-propyl)-amide (IXa)

A mixture of 5-chloro thiophen-2-carboxylic acid (39.2 g; 0.30 mol), dichloromethane (500 ml) and N,N-dimethylformamide (2.0 ml) was heated at 40-45° C. Thionyl chloride (40.2 g; 0.34 mol) was added to the reaction mixture at 40-45° C. for up to 1 hour and reaction was allowed to proceed further for 1 hour. Solvent was distilled out below 50° C. under vacuum to yield 5-chloro thiophene-2-carbonyl chloride (VIIIa). Dichloromethane (500 ml) was added to the -chloro thiophene-2-carbonyl chloride and stirred to make a clear solution. In another vessel, a mixture of (S)-4-{4-[N-benzyl-(3-amino-2-hydroxypropyl)amino]phenyl}morpholin-3-one (100 g; 0.28 mol), dichloromethane (500 ml) and triethylamine (42.7 ml; 0.42 mol) was cooled to 0-10° C. This mixture was added to the solution of 5-chloro thiophene-2-carbonyl chloride in dichloromethane at 0-10° C. within 1 to 2 hours and the reaction was allowed to proceed for 1 hour. After completion of the reaction, the reaction mixture was diluted with water (500 ml). The reaction mixture was allowed to stir at 25-35° C. for 20 min and then allowed to settle. The organic phase was separated and washed with aqueous sodium bicarbonate (25.0 g) solution in water (500 ml). Organic phase was distilled out below 50° C. under vacuum to yield title compound (130-140 g). Yield: 80.0-85.0%.

$^1$H NMR (DMSO) δ: 3.22-3.29 (1H, m), 3.33-3.38 (2H, m), 3.55-3.60 (3H, m), 3.90-3.92 (2H, q), 3.99-4.04 (1H, m), 4.12 (2H, s), 4.67 (2H, t), 5.18-5.20 (1Hd), 6.62-6.64 (2H, d), 7.01-7.04 (2H, d), 7.19-7.21 (4H, q), 7.28-7.32 (2H, m), 7.68-7.69 (1H, d), 8.66-8.69 (1H, t)

Mass: 501.1 [M+H]$^+$

Example 9

Preparation of (S)-5-chloro-thiophene-2-carboxylic acid (3-{N-benzyl-[4-(3-oxo-morpholin-4-yl)-phenyl]-amino}-2-hydroxy-propyl)-amide (IXa)

A mixture of 5-chloro thiophen-2-carboxylic acid (50.4 g; 0.31 mol), dichloromethane (300 ml) and N,N-dimethylformamide (2.0 ml) was heated at 40-45° C. A clear solution of thionyl chloride (45.7 g; 0.38 mol) in dichloromethane (200 ml) was added to the reaction mixture at 40-45° C. for 2-8 hours and stirred further for 1 hour. After completion of the reaction, the reaction solvent was distilled out below 50° C. atmospherically and then degassed under vacuum to get 5-chloro thiophene-2-carbonyl chloride. Dichloromethane (500 ml) was added to the 5-chloro thiophene-2-carbonyl chloride and stirred to make a clear solution. In another vessel, to a stirred solution of (S)-4-{4-[(3-amino-2-hydroxy-propyl)-benzyl-amino]-phenyl}-morpholin-3-one phosphate (100 g; 0.12 mol) in dichloromethane (500 ml), triethylamine (67.1 g; 0.66 mol) was added at 25-35° C. within 30-60 minutes and stirred further for 30 minutes. The clear solution of 5-chloro thiophene-2-carbonyl chloride in dichloromethane was added to the reaction mixture at 25-35° C. within 2-3 hours and reaction was allowed to proceed for 2 hours. After completion of reaction, the reaction mixture was diluted with water (500 ml). The reaction mixture was allowed to stir at 25-35° C. for 30 minutes and then allowed to settle. The organic phase was separated and washed with aqueous sodium bicarbonate (25.0 g) solution in water (500 ml) and water (500 ml), distilled out below 50° C. atmospherically, degassed under vacuum and stripped out of residual solvent with methanol (100 ml). The isolated solid was refluxed in methanol (600 ml) at 60-70° C. and stirred for 1 hour. The reaction mixture was cooled to 5-15° C. and stirred for 2 hours. Solid was filtered and washed with four times chilled (5-15° C.) methanol (25 ml). The solid was dried at 25-35° C. for 2 hours and then at 60-70° C. for 12 hours to give the title product (85-105 g).

Yield: 79.0%. HPLC Purity: 99.0%.

$^1$H NMR (DMSO) δ: 3.22-3.29 (1H, m), 3.33-3.38 (2H, m), 3.55-3.60 (3H, m), 3.90-3.92 (2H, q), 3.99-4.04 (1H, m), 4.12 (2H, s), 4.67 (2H, t), 5.18-5.20 (1Hd), 6.62-6.64 (2H, d), 7.01-7.04 (2H, d), 7.19-7.21 (4H, q), 7.28-7.32 (2H, m), 7.68-7.69 (1H, d), 8.66-8.69 (1H, t) Mass: 501.1 [M+H]$^+$

Example 10

Preparation of (S)-5-chloro-N-({(5S)-2-oxo-3-[4-(3-oxo-4-morpholinyl) phenyl]-1,3-oxazolidin-5-yl}methyl)-2-thiophenecarboxamide (Rivaroxaban) (I)

To a stirred solution of (S)-5-chloro-thiophene-2-carboxylic acid (3-{N-benzyl-[4-(3-oxo-morpholin-4-yl)-phenyl]-amino}-2-hydroxy-propyl)-amide (IXa) (5 g; 0.01 mol) in dichloromethane (25 ml), potassium carbonate was added (3.3 g; 0.024 mol) at 25-35° C. to give a heterogeneous reaction mixture. The mixture was cooled to 0-10° C. A solution of triphosgene (4.75 g; 0.016 mol) in dichloromethane (25 ml) was added to the reaction mixture at 0-10° C. within 30 minutes. The reaction was allowed to proceed at 25-35° C. for 8 hours. After completion of reaction, the mixture was cooled to 0-10° C. and diluted with water (25 ml). The solid was filtered and washed twice with water (2.5 ml) and then twice with dichloromethane (2.5 ml). The solid was dried at 25-35° C. to give the title product Rivaroxaban (3.6 g). Yield: 80.0%.

$^1$H NMR (DMSO) δ: 3.60-3.62 (2H, t), 3.70-3.72 (2H, t), 3.84-3.87 (1H, m), 3.96-3.98 (2H, m), 4.17-4.21 (3H, m), 4.81-4.88 (1H, m), 7.19-7.20 (1H, d), 7.39-7.42 (2H, m), 7.54-7.58 (2H, m), 7.69-7.70 (1H, d), 8.98-9.01 (1H, t) Mass: 436.1 [M+H]$^+$

Example 11

Preparation of 5-chloro-N-({(5S)-2-oxo-3-[4-(3-oxo-4-morpholinyl)phenyl]-1,3-oxazolidin-5-yl}methyl)-2-thiophenecarboxamide (Rivaroxaban) (I)

A solution of triphosgene (4.75 g; 0.016 mol) in dichloromethane (25 ml) was added to a mixture of (S)-4-(4-{3-[2-(5-Chloro-thiophen-2-yl)-2-oxo-ethylamino]-2-hydroxy-propylamino}-phenyl)-morpholin-3-one (IX') (5.0 g; 0.01 mol) in dichloromethane (25 ml) and cooled at 0-10° C. within 30 minutes. The reaction was allowed to proceed at 25-35° C. for 8 hours. After completion of the reaction, the reaction mixture was cooled to 0-10° C. and diluted with water (25 ml). An exotherm was observed. The reaction mixture was stirred at 25-35° C. for 1 hour. The solid was filtered and washed twice with water (2.5 ml) and then twice with dichloromethane (2.5 ml). The solid was dried at 25-35° C. to give the title product Rivaroxaban (I) (3.6 g). Yield: 82.7%.

Example 12

Preparation of 5-chloro-N-({(5S)-2-oxo-3-[4-(3-oxo-4-morpholinylphenyl]-1,3-oxazolidin-5-yl}methyl)-2-thiophenecarboxamide (Rivaroxaban) (I)

To a stirred solution of triphosgene (59.4 g; 0.20 mol) in dichloromethane (500 ml), a solution of (S)-5-chloro-thiophene-2-carboxylic acid (3-{benzyl-[4-(3-oxo-morpholin-4-yl)-phenyl]-amino}-2-hydroxy-propyl)-amide (100 g; 0.20 mol) in dichloromethane (500 ml) was added 25-35° C. for 2 to 3 hours and allowed to proceed for 16 hours. After completion of reaction, the reaction mixture was cooled to 0-10° C. Liquor ammonia (20-25% w/w) (144.5 g; 1.70 mol) was added to the reaction mixture at 0-10° C. within 2-3 hours. The pH (6 to 8) of the reaction mixture was adjusted by the addition of glacial acetic acid (approx. 18 g) at below 20° C. Solvent was distilled out below 50° C. atmospherically. The isolated solid was heated in methanol (400 ml) at 45-55° C. and stirred further for 1 hour. The reaction mixture was cooled to 25-35° C. and stirred further for 1 hour. The solid was filtered and washed with methanol (25 ml×4) and the slurry washed with water (1000 ml). The solid was dried at 45-55° C. under vacuum for 8-12 hours then at 45-55° C. 12 hours to give the title product (55-75 g). Yield: 66.0%. HPLC Purity: 98.0%.

Example 13

Preparation of 5-chloro-N-({(5S)-2-oxo-3-[4-(3-oxo-4-morpholinylphenyl]-1,3-oxazolidin-5-yl}methyl)-2-thiophenecarboxamide (Rivaroxaban) (I)

A mixture of 5-chloro-N-[2-oxo-3-[4-(3-oxomorpholin-4-yl) phenyl]oxazolidin-5(S)-ylmethyl]thiophene-2-carboxamide (100.0 g; 0.23 mol) and glacial acetic acid (500.0 ml) was heated at 60-70° C. and stirred for 1 hour. The reaction mixture cooled to 20-30° C. and stirred for 2 hours. The resulting solid was filtered and washed with glacial acetic acid (25 ml×4). The isolated solid was dissolved in glacial acetic acid (1800 ml) at 80-85° C., filtered through a fine filter pad and washed with hot glacial acetic acid (25 ml×4). The reaction mixture was cooled to 20-30° C. for 2 hours. The resulting solid was filtered, washed with glacial acetic acid (25 ml×4) and the slurry washed two times in water at 45-55° C. The filtered solid was dried at 25-35° C. for 2 hours, at 35-45° C. for 2 hours and then at 45-55° C. for 12 hours to give the title product (55-75 g). Yield: 61.0%. HPLC Purity: 99.9%.

1H NMR (DMSO) δ: 3.60-3.62 (2H, t), 3.70-3.72 (2H, t), 3.84-3.87 (1H, m), 3.96-3.98 (2H, m), 4.17-4.21 (3H, m), 4.81-4.88 (1H, m), 7.19-7.20 (1H, d), 7.39-7.42 (2H, m), 7.54-7.58 (2H, m), 7.69-7.70 (1H, d), 8.98-9.01 (1H, t)

Mass: 436.1 [M+H]+

We claim:

1. A process for the preparation of Rivaroxaban (I)

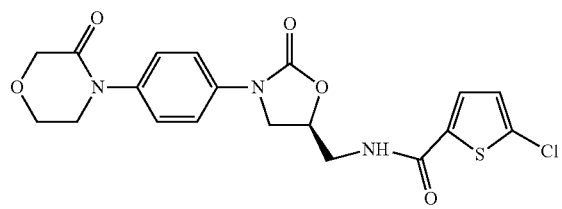

(I)

comprising:
a) reacting a compound of formula (IV)

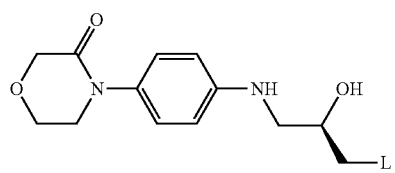

(IV)

with a compound G-L of formula (V), optionally in the presence of a suitable base to give a compound of formula (VI)

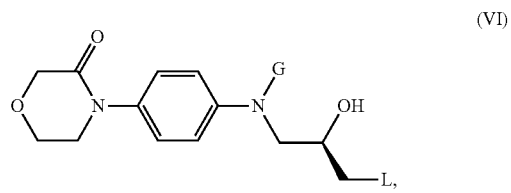

(VI)

wherein L is a leaving group and G is a protecting group;

b) converting the compound of formula (VI) to a compound of formula (VII) or salt thereof which may optionally involve isolation of a compound of formula (VII')

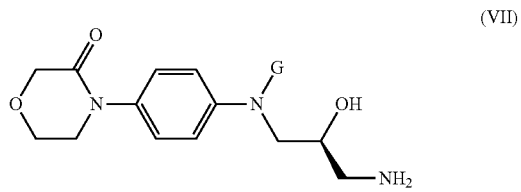

(VII)

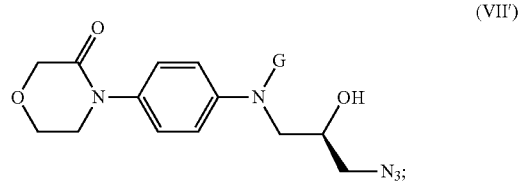

(VII')

c) reacting the compound of formula (VII) or salt thereof with 5-chloro thiophen-2-carboxylic acid of formula (VIII)

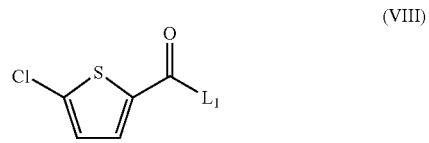

(VIII)

in the presence of a suitable base to give a compound of formula (IX)

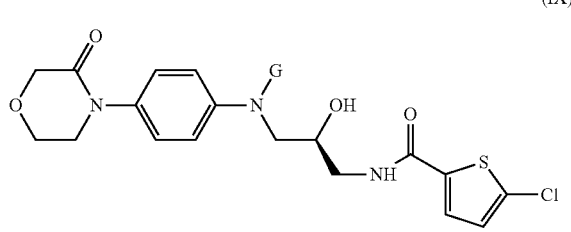

(IX)

wherein $L_1$ is a leaving group; and d) deprotecting and cyclizing the compound of formula (IX) to provide Rivaroxaban (I).

2. The process of claim 1, wherein the base used in step (a) is selected from the group consisting of DIPEA (diisopropylethyl amine), TEA (triethyl amine), DEA (diethyl amine), pyridine, DBU (1,8-Diazabicyclo[5.4.0]undec-7-ene), imidazole, N,N-dimethyl aniline, DMAP (4-Dimethylaminopyridine), and mixtures thereof.

3. The process of claim 2, wherein the base used in step (a) is DIPEA.

4. The process of claim 1, wherein step (b) involves reaction of compound (VI) with an alkali azide followed by reduction with triphenylphosphine.

5. The process of claim 1, wherein the base used in step (c) is selected from the group consisting of DIPEA (diisopropylethyl amine), TEA (triethyl amine), DEA (diethyl amine), pyridine, DMAP (4-Dimethylaminopyridine), DBU (1,8-Diazabicyclo[5.4.0]undec-7-ene), N,N-dimethyl aniline, potassium carbonate, sodium carbonate, lithium carbonate, sodium bicarbonate, potassium bicarbonate, lithium bicarbonate, and mixtures thereof.

6. The process of claim 1, wherein deprotection and cyclization of step (d) is performed using a phosgene equivalent selected from the group consisting of triphosgene, carbonyl diimidazole (CDI), dicyclohexyl carbodiimide (DCC), and mixtures thereof.

7. The process of claim 6, wherein deprotection and cyclization of step (d) is performed using triphosgene.

8. A process for the preparation of Rivaroxaban (I)

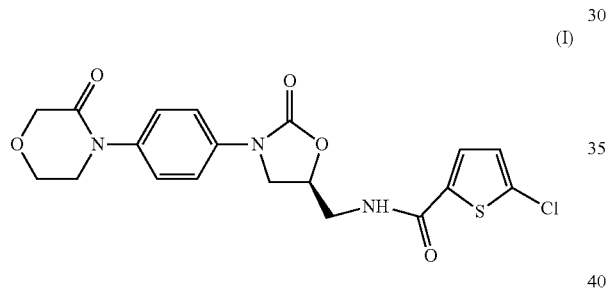

(I)

comprising:

a) reacting (R)-4-[4-(3-chloro-2-hydroxypropylamino)-phenyl]-morpholin-3-one (IVa)

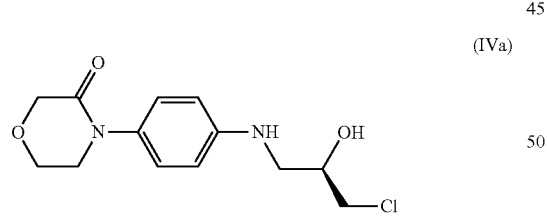

(IVa)

with benzyl bromide (Va) or benzyl chloride (Va')

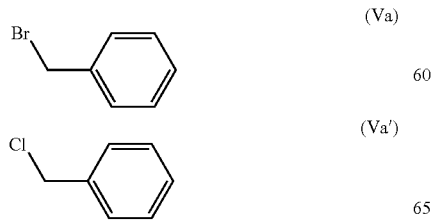

(Va)

(Va')

optionally, in the presence of a suitable base, to give (R)-4-{4-[N-benzyl-(3-chloro-2-hydroxypropyl)amino]phenyl}-morpholin-3-one (VIa)

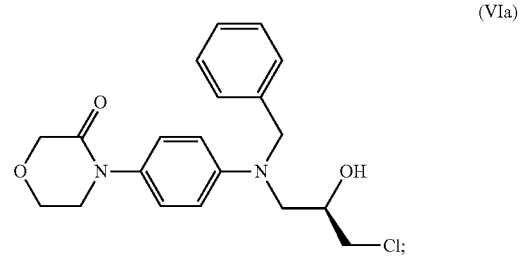 [SMILES: O=C1COCCN1c1ccc(N(Cc2ccccc2)C[C@@H](O)CCl)cc1]

(VIa)

b) converting (R)-4-{4-[N-benzyl-(3-chloro-2-hydroxypropyl)amino]phenyl}-morpholin-3-one (VIa) to (S)-4-{4-[N-benzyl-(3-amino-2-hydroxypropyl)amino]phenyl}-morpholin-3-one phosphate (VIIaa) which may optionally involve isolation of (R)-4-{4-[N-benzyl-(3-azido-2-hydroxypropyl)amino]-phenyl}-morpholin-3-one (VII'a)

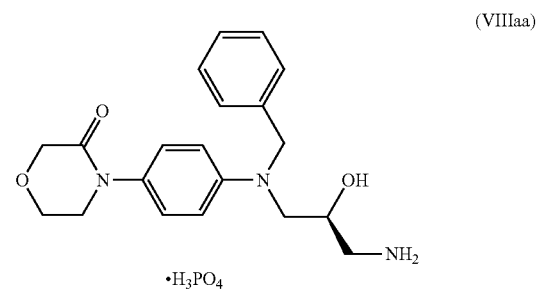

(VIIaa)

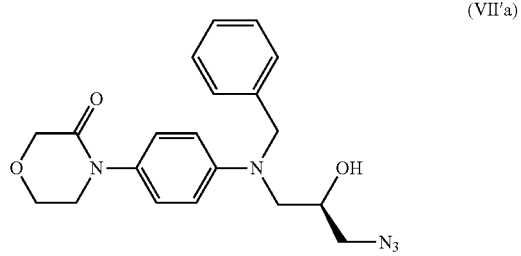

(VII'a)

c) reacting compound of formula (VIIa) with 5-chlorothiophene-2-carbonyl chloride (VIIIa)

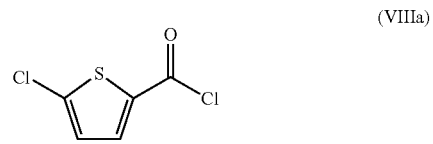

(VIIIa)

in the presence of a suitable base to give the compound of formula (IXa)

10. A compound selected from:
(IXa)
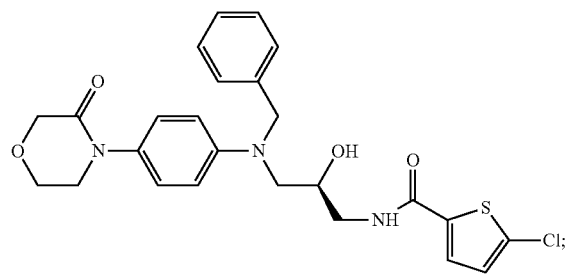
and
d) deprotecting and cyclizing compound of formula (IXa) to provide Rivaroxaban (I).
9. A compound selected from:
(VIa)
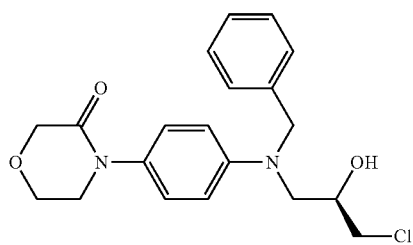
(VII′a)
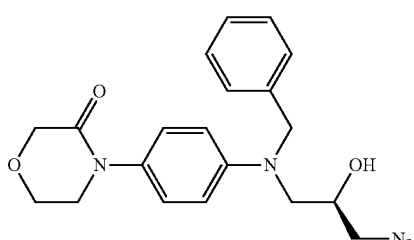
(VI)
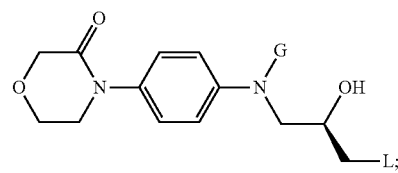
(VIIa)
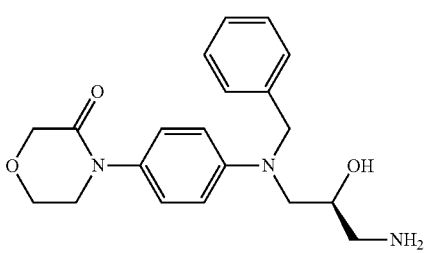
(VII′)
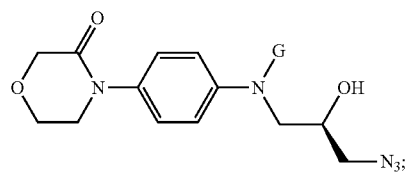
(VIIaa)
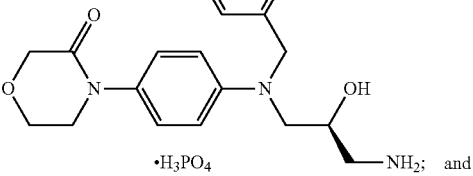
(VII)
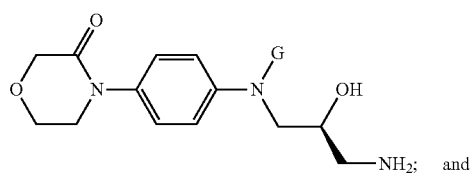
·H$_3$PO$_4$  and
(IXa)
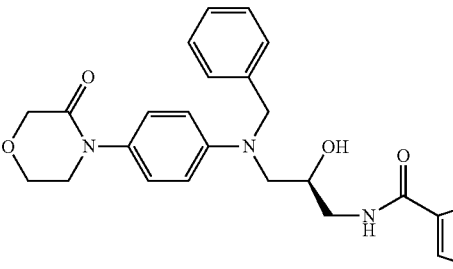
(IX)
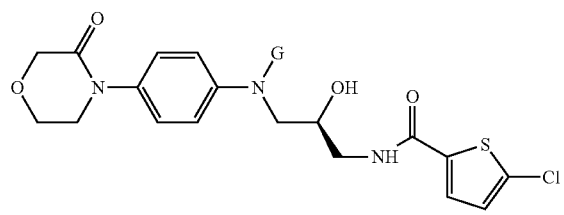
wherein G is a protecting group and L is a leaving group.
* * * * *